(12) United States Patent
Tatsumi et al.

(10) Patent No.: US 10,612,150 B2
(45) Date of Patent: Apr. 7, 2020

(54) SNAG ALLOY PLATING SOLUTION

(71) Applicant: MITSUBISHI MATERIALS CORPORATION, Tokyo (JP)

(72) Inventors: Koji Tatsumi, Sanda (JP); Tsukasa Yasoshima, Sanda (JP); Takuma Katase, Sanda (JP)

(73) Assignee: MITSUBISHI MATERIALS CORPORATION, Tokyo (JP)

( * ) Notice: Subject to any disclaimer, the term of this patent is extended or adjusted under 35 U.S.C. 154(b) by 25 days.

(21) Appl. No.: 16/066,126

(22) PCT Filed: Dec. 21, 2016

(86) PCT No.: PCT/JP2016/088102
§ 371 (c)(1),
(2) Date: Jun. 26, 2018

(87) PCT Pub. No.: WO2017/115701
PCT Pub. Date: Jul. 6, 2017

(65) Prior Publication Data
US 2019/0338433 A1  Nov. 7, 2019

(30) Foreign Application Priority Data

Dec. 28, 2015  (JP) ................................ 2015-256577
Nov. 30, 2016  (JP) ................................ 2016-232903

(51) Int. Cl.
*C25D 3/56* (2006.01)
*C25D 3/60* (2006.01)
*C07D 403/12* (2006.01)
*C07D 257/04* (2006.01)

(52) U.S. Cl.
CPC ............. *C25D 3/56* (2013.01); *C07D 403/12* (2013.01); *C07D 257/04* (2013.01)

(58) Field of Classification Search
CPC .................................... C25D 3/60; C25D 3/64
USPC .................................................. 205/238, 253
See application file for complete search history.

(56) References Cited

U.S. PATENT DOCUMENTS

| | | | |
|---|---|---|---|
| 8,888,984 B2 | 11/2014 | Lee et al. | |
| 2013/0206602 A1 | 8/2013 | Lee et al. | |
| 2014/0353162 A1* | 12/2014 | Foyet .................. | C25D 5/505 |
| | | | 205/122 |
| 2015/0240375 A1 | 8/2015 | Foyet et al. | |

FOREIGN PATENT DOCUMENTS

| | | |
|---|---|---|
| CN | 1896334 A | 1/2007 |
| CN | 103361685 A | 10/2013 |
| CN | 104911648 A | 9/2015 |
| JP | 11-269691 A | 10/1999 |
| JP | 2003-084406 A | 3/2003 |
| JP | 2013-167019 A | 8/2013 |
| JP | 2014-122410 A | 7/2014 |
| JP | 2015-092022 A | 5/2015 |
| JP | 2015-158012 A | 9/2015 |
| TW | 201245047 A | 11/2012 |
| WO | 2010/074067 A1 | 7/2010 |
| WO | 2014/165867 A1 | 10/2014 |

OTHER PUBLICATIONS

Office Action dated Jun. 13, 2018, issued for the Taiwanese patent application No. 105142781 and English translation thereof.
Notice of Allowance dated Feb. 11, 2019, issued for the Chinese patent application No. 201680076384.2 and English translation thereof.
International Search Report dated Feb. 14, 2017, issued for PCT/JP2016/088102 and English translation thereof.

* cited by examiner

*Primary Examiner* — Edna Wong
(74) *Attorney, Agent, or Firm* — Locke Lord LLP

(57) ABSTRACT

The SnAg alloy plating solution of the invention is a SnAg alloy plating solution including a water-soluble tin compound, a water-soluble silver compound, and a particular sulfide compound in an amount in the range of 0.25 mol or more and 10 mol or less with respect to 1 mol of silver in the water-soluble silver compound.

5 Claims, No Drawings ns to a SnAg alloy plating solution for forming a plating film of a SnAg alloy containing tin and silver.

Priority is claimed on Japanese Patent Application No. 2015-256577, filed on Dec. 28, 2015, and Japanese Patent Application No. 2016-232903, filed on Nov. 30, 2016, the contents of which are incorporated herein by reference.

BACKGROUND ART

SnAg alloy solder is used as a PbSn solder substitute material in bonding materials for use in semiconductor substrates (wafers) or printed boards. An SnAg alloy plating solution for forming a SnAg alloy by a plating method is formed of an aqueous solution obtained by dissolving a tin compound and a silver compound. When tin or silver dissolved in this SnAg alloy plating solution is precipitated into the plating solution as metal or an insoluble salt, the alloy composition of the SnAg alloy plating film formed on an object to be plated will not become the composition as planned, and the precipitate causes defective gloss or uneven gloss of the plating film. In the SnAg alloy plating solution, since silver is a more noble metal than tin, an oxidation reaction of $Sn^{2+}$ ions and a reduction reaction of $Ag^+$ ions occur in the plating solution, and silver tends to be easily precipitated out. Therefore, in order to stably dissolve the silver compound in the SnAg alloy plating solution, a sulfur-containing compound such as a heterocyclic compound having a mercapto group or a sulfide compound is added as a complexing agent to the solution, and thereby a complex of silver is formed.

Patent Document 1 discloses a plating solution including a nitrogen-containing heterocyclic compound substituted with a mercapto group. In this Patent Document 1, 1-(2-dimethylaminoethyl)-5-mercapto-1,2,3,4-tetrazole is listed as an example of the nitrogen-containing heterocyclic compound.

Patent Document 2 discloses a plating solution including a mercaptotetrazole derivative and dithiaalkyl diol.

Patent Document 3 discloses a plating solution including a particular sulfide-based compound such as 2,2'-dipyridyl sulfide or 2,2'-dipiperazinyl disulfide, which has one or more basic nitrogen atoms in the molecule, and a plating solution including a particular thio crown ether compound such as 1-aza-7-oxa-4,10-dithiacyclododecane.

Patent Document 4 discloses a plating solution including a sulfur-containing compound that has a particular monocyclic heterocyclic group or fused heterocyclic group, both of which contains 1 to 5 units of at least one atom selected from nitrogen, sulfur, and oxygen, and has a sulfide group or a mercapto group adjacent to the heterocyclic group.

CITATION LIST

Patent Document

[Patent Document 1] U.S. Pat. No. 8,888,984
[Patent Document 2] Japanese Unexamined Patent Application, First Publication No. 2015-92022 (Examples)
[Patent Document 3] Japanese Unexamined Patent Application, First Publication No. H11-269691
[Patent Document 4] Japanese Unexamined Patent Application, First Publication No. 2014-122410

SUMMARY OF INVENTION

Technical Problem

A SnAg alloy plating solution is desirable such that even if the plating solution is used or stored for a long time period, the SnAg alloy plating solution is capable of stably forming a SnAg alloy plating film. However, when conventional SnAg alloy plating solutions including sulfur-containing compounds are used or stored for a long time period, silver is precipitated out as metal or an insoluble salt in the plating solution, and it may become difficult for the plating solution to form a SnAg alloy plating film stably. For example, the heterocyclic compound having a mercapto group as shown in Patent Document 1 is highly water-soluble; however, since the compound has only a single sulfur atom in the molecule, the effect of forming a complex of silver tends to be low. The dithiaalkyl diol shown in Patent Document 2 has two sulfur atoms in the molecule and has therefore a superior effect of forming a complex of silver; however, the compound is likely to undergo self-decomposition in water, and there have been occasions in which water-solubility of the compound becomes poor. Patent Document 3 describes a sulfide-based compound having two or more sulfur atoms and a thio crown ether compound, and Patent Document 4 describes a sulfur-containing compound having two or more sulfur atoms. However, the sulfur-containing compounds shown in these Patent Documents tend to have low water-solubility.

This invention was achieved in view of such circumstances as shown above, and it is an object of the invention to provide a SnAg alloy plating solution, in which silver is not easily precipitated out as metal or an insoluble salt in the plating solution even if the plating solution is used or stored for a long time period, and which is capable of stably forming a SnAg alloy plating film.

Solution to Problem

In order to solve the problems shown above, the SnAg alloy plating solution according to an aspect of the present invention is a SnAg alloy plating solution including a water-soluble tin compound, a water-soluble silver compound, and a sulfide compound in an amount in the range of 0.25 mol or more and 10 mol or less with respect to 1 mol of silver in the water-soluble silver compound, and the sulfide compound is a compound represented by the following Formula (I) or Formula (II):

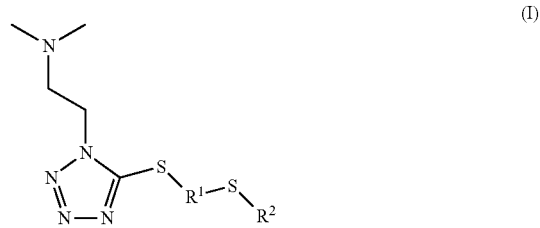

(I)

In Formula (I), $R^1$ represents a single bond or a divalent linking group; and $R^2$ represents one selected from the group consisting of a hydrogen atom, an alkyl group, a hydroxyalkyl group, an aryl group, an aralkyl group, and an alkoxy group.

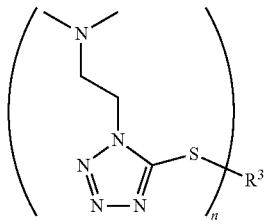

(II)

In Formula (II), n represents a number from 2 to 4; and $R^3$ represents an n-valent linking group.

When a SnAg alloy plating solution of this configuration is used, since the sulfide compound represented by Formula (I) or Formula (II) is included in an amount of 0.25 mol or more with respect to 1 mol of silver in the water-soluble silver compound, even if the plating solution is used or stored for a long time period, silver is not easily precipitated out as metal or an insoluble salt in the plating solution, and a SnAg alloy plating film can be stably formed. That is, the sulfide compound of Formula (I) or Formula (II) has two or more sulfur atoms that are easily coordinated with silver in the molecule, and also has a tetrazole group having a dimethylaminoalkyl group having superior water-solubility. Therefore, the sulfide compounds of Formula (I) and Formula (II) are easily dissolved in the SnAg alloy plating solution and can easily form stable complexes by being coordinated with silver. Therefore, it is considered that in the SnAg alloy plating solution of the present invention, silver exists in an aqueous solution as a stable complex for a long time period, and silver is not easily precipitated out as metal or an insoluble salt in the plating solution.

Furthermore, since the amount of the sulfide compound is adjusted to be 10 mol or less with respect to 1 mol of silver in the water-soluble silver compound, at the time of forming a SnAg alloy plating film, silver can be stably electrodeposited together with tin on an object to be plated. Therefore, it is possible to form a SnAg alloy plating film stably.

In regard to the SnAg alloy plating solution according to the aspect of the present invention, in a case in which the sulfide compound is a compound represented by Formula (I), it is preferable that $R^1$ represents a single bond or a divalent linking group, and $R^1$ as a divalent linking group is a divalent linking group selected from the group consisting of a hydrocarbon group with or without a substituent, a heterocyclic group with or without a substituent, a carbonyl group (—CO—), an oxy group (—O—), an imino group with or without a substitution with an alkyl group having a number of carbon atoms in the range of 1 to 8 (—NR—; provided that R represents a hydrogen atom or an alkyl group having a number of carbon atoms in the range of 1 to 8), a thio group (—S—), a sulfinyl group (—SO—), a sulfonyl group (—SO$_2$—), a —PO$_2$— group, and groups obtained by combining these groups.

When a SnAg alloy plating solution having this configuration is used, since the sulfide compound is highly water-soluble, a reliably stable complex of silver can be formed.

In regard to the SnAg alloy plating solution according to the aspect of the present invention, in a case in which the sulfide compound is a compound represented by Formula (II) and n is 2, it is preferable that $R^3$ as a divalent linking group is a divalent linking group selected from the group consisting of a hydrocarbon group with or without a substituent, a heterocyclic group with or without a substituent, a carbonyl group (—CO—), an oxy group (—O—), an imino group with or without a substitution with an alkyl group having a number of carbon atoms in the range of 1 to 8 (—NR—; provided that R represents a hydrogen atom or an alkyl group having a number of carbon atoms in the range of 1 to 8), a thio group (—S—), a sulfinyl group (—SO—), a sulfonyl group (—SO$_2$—), a —PO$_2$— group, and groups obtained by combining these.

When a SnAg alloy plating solution of this configuration is used, since the sulfide compound is highly water-soluble, a reliably stable complex of silver can be formed.

In regard to the SnAg alloy plating solution according to the aspect of the present invention, in a case in which the sulfide compound is a compound represented by Formula (II) and n is 3, it is preferable that $R^3$ is a trivalent linking group or a group obtained by combining a trivalent linking group and a divalent linking group.

When a SnAg alloy plating solution of this configuration is used, since the sulfide compound is highly water-soluble, a reliably stable complex of silver can be formed.

In regard to the SnAg alloy plating solution according to the aspect of the present invention, in a case in which the sulfide compound is a compound represented by Formula (II) and n is 4, it is preferable that $R^3$ is a tetravalent linking group or a group obtained by combining a tetravalent linking group and a divalent linking group.

When a SnAg alloy plating solution of this configuration is used, since the sulfide compound is highly water-soluble, a reliably stable complex of silver can be formed.

Advantageous Effects of Invention

As shown above, according to the present invention, a SnAg alloy plating solution can be provided, in which even if the plating solution is used or stored for a long time period, silver is not easily precipitated out as metal or an insoluble salt in the plating solution, and which can stably form a SnAg alloy plating film.

DESCRIPTION OF EMBODIMENTS

Hereinafter, the SnAg alloy plating solution according to embodiments of the present invention will be explained.

The SnAg alloy plating solution according to the present embodiment is utilized as a plating solution for forming a SnAg alloy plating film on an object to be plated, such as a semiconductor substrate or a printed board. The SnAg alloy plating film is utilized as SnAg alloy solder, which is a bonding material for a semiconductor substrate or a printed board.

The SnAg alloy plating solution of the present embodiment includes a water-soluble tin compound, a water-soluble silver compound, and a particular sulfide compound.

The water-soluble tin compound used for the SnAg alloy plating solution of the present embodiment is a compound that dissolves in water and produces divalent tin ion. Examples of the water-soluble tin compound may include halides, sulfate, oxide, alkanesulfonates, arylsulfonates, and alkanol sulfonates of tin. Specific examples of the alkanesulfonates may include methanesulfonate and ethanesulfonate. Specific examples of the arylsulfonates may include benzenesulfonate, phenolsulfonate, cresolsulfonate, and toluenesulfonate. Specific examples of the alkanol sulfonates may include isethionate. The water-soluble tin compounds may be used singly, or two or more kinds thereof may be used in combination. The amount of the water-soluble tin compound in the SnAg alloy plating solution of the present embodiment is, in terms of the amount of tin, generally in the range of 1 g/L or more and 200 g/L or less, preferably in the range of 10 g/L or more and 120 g/L or less, and more preferably in the range of 20 g/L or more and 100 g/L or less.

Examples of the water-soluble silver compound used for the SnAg alloy plating solution of the present embodiment may include halides, sulfate, oxide, alkanesulfonates, arylsulfonates, and alkanol sulfonates of silver. Specific examples of the alkanesulfonates, arylsulfonates, and alkanol sulfonates are the same as the compounds mentioned above as examples of the water-soluble tin compound. The water-soluble silver compounds may be used singly, or two or more kinds thereof may be used in combination. The amount of the water-soluble tin compound in the SnAg alloy plating solution of the present embodiment is, in terms of the amount of silver, generally in the range of 0.01 g/L or more and 20 g/L or less, preferably in the range of 0.1 g/L or more 10 g/L or less, and more preferably in the range of 0.1 g/L or more and 5 g/L or less.

The SnAg alloy plating solution of the present embodiment may further include a water-soluble compound of a metal other than tin and silver. Examples of the metal other than tin and silver include gold, copper, bismuth, indium, zinc, antimony, and manganese. Examples of the water-soluble compound of the above-mentioned metal include halides, sulfate, oxide, alkanesulfonates, arylsulfonates, and alkanol sulfonates of the metal. Specific examples of the alkanesulfonates, arylsulfonates, and alkanol sulfonates are the same as the compounds mentioned as examples of the water-soluble tin compound. The water-soluble compounds of a metal other than tin and silver may be used singly, or two or more kinds thereof may be used in combination. The amount of the water-soluble compound of a metal other than tin and silver in the SnAg plating solution of the present embodiment is generally in the range of 0.01 g/L or more and 20 g/L or less, preferably in the range of 0.1 g/L or more 10 g/L or less, and more preferably in the range of 0.1 g/L or more and 5 g/L or less.

The sulfide compound used for the SnAg alloy plating solution of the present embodiment is a compound represented by the following Formula (I) or Formula (II).

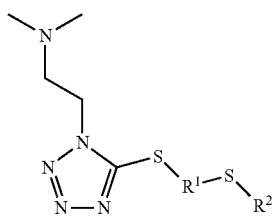

(I)

In Formula (I), $R^1$ represents a single bond or a divalent linking group. Examples of the divalent linking group include a hydrocarbon group with or without a substituent, a heterocyclic group with or without a substituent, a carbonyl group (—CO—), an oxy group (—O—), an imino group with or without a substitution with an alkyl group having a number of carbon atoms in the range of 1 to 8 (—NR—; provided that R represents a hydrogen atom or an alkyl group having a number of carbon atoms in the range of 1 to 8), a thio group (—S—), a sulfinyl group (—SO—), a sulfonyl group (—$SO_2$—), a —$PO_2$— group, and groups obtained by combining these.

The hydrocarbon group includes an unsaturated hydrocarbon group and a saturated hydrocarbon group. The hydrocarbon group includes a linear hydrocarbon group which may be branched, and a cyclic hydrocarbon group. Examples of the hydrocarbon group include an alkylene group having a number of carbon atoms in the range of 1 to 8, an alkenylene group having a number of carbon atoms in the range of 2 to 8, an alkynylene group having a number of carbon atoms in the range of 2 to 8, and an arylene group having a number of carbon atoms in the range of 6 to 18. Specific examples of the alkylene group include linear alkylene groups such as a methylene group, an ethylene group, a trimethylene group, a tetramethylene group, a hexamethylene group, and an octamethylene group; and cyclic alkylenes such as a cyclopropylene group, a cyclobutylene group, a cyclopentylene group, a cyclohexylene group, a cycloheptylene group, and a cyclooctylene group, all of which may respectively have a substituent. Specific examples of the alkenylene group include an ethenylene group and a propenylene group, all of which may respectively have a substituent. Specific examples of the alkynylene group include an ethynylene group and a propynylene group, all of which may respectively have a substituent. Specific examples of the arylene group include a phenylene group and a naphthylene group, all of which may respectively have a substituent.

An example of the heterocyclic group may be a group obtained by eliminating two hydrogen atoms from an aromatic or aliphatic heterocyclic compound containing a nitrogen atom, an oxygen atom, a sulfur atom, or a phosphorus atom. Specific examples of the aromatic heterocyclic compound include pyrrole, imidazole, pyrazole, furan, oxazole, isoxazole, thiophene, thiazole, isothiazole, pyridine, pyrimidine, pyridazine, pyrazine, 1,2,3-triazine, quinoline, isoquinoline, quinazoline, phthaladine, pteridine, coumarin, chromone, 1,4-benzazepine, indole, benzimidazole, benzofuran, purine, acridine, phenoxazine, and phenothiazine, all of which may respectively have a substituent. Specific examples of the aliphatic heterocyclic compound include piperidine, piperazine, morpholine, quinuclidine, pyrrolidine, azetidine, octacene, azetidin-2-one, and tropane all of which may respectively have a substituent.

Examples of the substituent of the hydrocarbon group and the heterocyclic group include a halogen atom, a hydroxyl group, an amino group, an alkyl group, an aryl group, an aralkyl group, and an alkoxy group. Specific examples of the halogen atom include fluorine and chlorine. It is preferable that the alkyl group has the number of carbon atoms in the range of 1 to 8. The alkyl group includes a linear alkyl group and a cyclic alkyl group. Specific examples of the alkyl group include linear alkyl groups such as a methyl group, an ethyl group, an n-propyl group, an isopropyl group, an n-butyl group, and an isobutyl group; and cyclic alkyl groups such as a cyclopropyl group, a cyclobutyl group, a cyclopentyl group, and a cyclohexyl group. It is preferable that the aryl group has the number of carbon atoms in the range of 6 to 18. Specific examples of the aryl group include a phenyl group and a naphthyl group. It is preferable that the aralkyl group has the number of carbon atoms in the range of 7 to 30. Specific examples of the aralkyl group include a benzyl group, a phenethyl group, a naphthylmethyl group, and naphthylethyl. It is preferable that the alkoxy group has the number of carbon atoms in the range of 1 to 8. Specific examples of the alkoxy group include a methoxy group, an ethoxy group, a hydroxyethoxy group, a propoxy group, a hydroxypropoxy group, and a butoxy group.

Examples of a group obtained by combining the linking groups include groups having —CO—, —O—, —NR—, —S—, —SO—, —SO$_2$—, —PO$_2$—, —CO—O—, or —CO—NR— between divalent hydrocarbon groups. A group obtained by combining a divalent hydrocarbon group and —S— includes a polysulfide group having a number of sulfur atoms in the range of 2 to 5.

$R^2$ represents a hydrogen atom, an alkyl group, a hydroxyalkyl group, an aryl group, an aralkyl group, or an alkoxy group. The alkyl group includes a linear alkyl group which may be branched, and a cyclic alkyl group. It is preferable that the alkyl group has the number of carbon atoms in the range of 1 to 8. A hydroxyalkyl group means an alkyl group in which a hydroxyl group is bonded to a terminal carbon atom thereof. It is preferable that the alkyl group of the hydroxyalkyl group has a number of carbon atoms in the range of 1 to 8. It is preferable that the aryl group has a number of carbon atoms in the range of 6 to 18. It is preferable that the aralkyl group has a number of carbon atoms in the range of 7 to 18. It is preferable that the alkoxy group has a number of carbon atoms in the range of 1 to 8. Specific examples of the alkyl group, aryl group, aralkyl group and alkoxy group are similar to the groups mentioned as examples of the substituent for the hydrocarbon group and heterocyclic group represented by $R^1$.

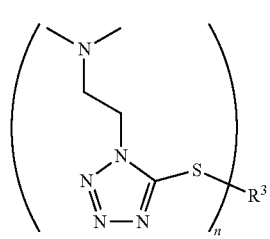

(II)

In Formula (II), n represents a number from 2 to 4; and $R^3$ represents an n-valent linking group.

In a case in which n is 2, $R^3$ represents a divalent linking group. Examples of the divalent linking group are similar to the divalent linking groups mentioned in the case of $R^1$ of Formula (I).

In a case in which n is 3, $R^3$ represents a trivalent linking group or a group obtained by combining a trivalent linking group and a divalent linking group. Examples of the trivalent linking group include a hydrocarbon group with or without a substituent, and a heterocyclic group which may have a substituent. Examples of the divalent linking group are similar to the divalent linking groups mentioned in the case of $R^1$ of Formula (I).

An example of the trivalent hydrocarbon group with or without a substituent may be a group obtained by eliminating three hydrogen atoms from a hydrocarbon compound which may have a substituent. The hydrocarbon compound includes an unsaturated hydrocarbon compound and a saturated hydrocarbon compound. The hydrocarbon compound includes a linear hydrocarbon compound which may be branched, and a cyclic hydrocarbon compound. Examples of the hydrocarbon compound include an alkane having a number of carbon atoms in the range of 1 to 8, an alkene having a number of carbon atoms in the range of 2 to 8, an alkyne having a number of carbon atoms in the range of 2 to 8, and an aromatic hydrocarbon having a number of carbon atoms in the range of 6 to 18. Specific examples of the alkane include linear alkanes such as methane, ethane, and propane; and cycloalkanes such as cyclopropane, cyclobutane, cyclopentane, cyclohexane, cycloheptane, and cyclooctane, all of which may respectively have a substituent. Specific examples of the alkene include ethylene and propylene, all of which may respectively have a substituent. Specific examples of the alkyne include acetylene and propyne, all of which may respectively have a substituent.

An example of the trivalent heterocyclic group which may have a substituent may be a group obtainable by eliminating three hydrogen atoms from a heterocyclic compound. Examples of the heterocyclic compound are similar to the compounds mentioned as examples of heterocyclic compounds that form the divalent heterocyclic group of $R^1$ of Formula (I) (provided that heterocyclic compounds having a number of hydrogen atoms of 2 or less are excluded).

Examples of the substituent for the trivalent hydrocarbon group and the trivalent heterocyclic group include a halogen atom, a hydroxyl group, an amino group, an alkyl group, an aryl group, an aralkyl group, and an alkoxy group. Specific examples of the halogen atom, the alkyl group, the aryl group, the aralkyl group, and the alkoxy group are similar to the groups mentioned as examples of the substituent for the hydrocarbon group and heterocyclic group represented by $R^1$ of Formula (I).

Examples of $R^3$ in the case where n is 3 include the groups represented by the following Formula (III).

(III)

In Formula (III), $R^4$, $R^5$, and $R^6$ each independently represent a single bond or a divalent linking group. Examples of the divalent linking group are similar to the divalent linking groups for $R^1$ of Formula (I).

In a case in which n is 4, $R^3$ represents a tetravalent linking group or a group obtained by combining a tetravalent linking group and a divalent linking group. Examples of the tetravalent linking group include a hydrocarbon group with or without a substituent, and a heterocyclic group which may have a substituent. Examples of the divalent linking group are similar to the divalent linking groups mentioned in the case of $R^1$ of Formula (I).

An example of the tetravalent hydrocarbon group with or without a substituent may be a group obtainable by eliminating four hydrogen atoms from a hydrocarbon compound which may have a substituent. Examples of the hydrocarbon compound are similar to the compounds mentioned as examples of the hydrocarbon compound that forms a trivalent hydrocarbon group.

An example of the tetravalent heterocyclic group which may have a substituent may be a group obtainable by eliminating four hydrogen atoms from a heterocyclic compound. Examples of the heterocyclic compound are similar to the compounds mentioned as examples of the heterocyclic compound that forms the divalent heterocyclic group of $R^1$ of Formula (I) (provided that heterocyclic compounds having a number of hydrogen atoms of 3 or less are excluded).

Examples of the substituent for the tetravalent hydrocarbon group and the tetravalent heterocyclic group include a halogen atom, a hydroxyl group, an amino group, an alkyl group, an aryl group, an aralkyl group, and an alkoxy group. Specific examples of the halogen atom, the alkyl group, the aryl group, the aralkyl group, and the alkoxy group are similar to the groups mentioned as examples of the substituent for the hydrocarbon group and the heterocyclic group represented by $R^1$ of Formula (I).

An example of $R^3$ in the case where n is 4 may be a group represented by the following Formula (IV).

In Formula (IV), $R^7$, $R^8$, $R^9$, and $R^{10}$ each independently represent a single bond or a divalent linking group. The divalent linking group is similar to $R^1$ of Formula (I).

The sulfide compound of Formula (I) can be synthesized by, for example, a method of subjecting a sulfur-containing alcohol having one or more sulfur atoms and 1-(2-dimethylaminoethyl)-5-mercaptotetrazole as dehydration condensation. Furthermore, the sulfide compound can also be synthesized by a method of reacting a halide having one or more sulfur atoms and having one halogen atom, with 1-(2-dimethylaminoethyl)-5-mercaptotetrazole under basic conditions.

Examples of the sulfur-containing alcohol include the following compounds.

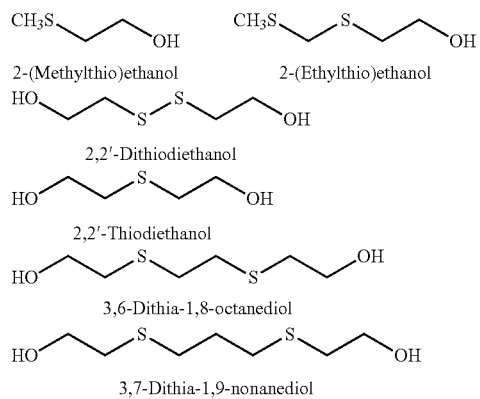

The sulfide compound of Formula (II) can be synthesized by, for example, a method of subjecting an n-hydric alcohol and 1-(2-dimethylaminoethyl)-5-mercaptotetrazole to dehydration condensation. Furthermore, the sulfide compound can also be synthesized by a method of reacting a halide having n units of a halogen atom with 1-(2-dimethylaminoethyl)-5-mercaptotetrazole under basic conditions.

In regard to the SnAg alloy plating solution of the present embodiment, the sulfide compounds shown above may be used singly, or two or more kinds thereof may be used in combination. The amount of the sulfide compound in the SnAg alloy plating solution of the present embodiment is an amount of 0.25 mol or more, and preferably 0.5 or more, with respect to 1 mol of silver in the water-soluble silver compound including the SnAg alloy plating solution. When the amount of the sulfide compound is too small, there is a risk that silver may be easily precipitated out. Meanwhile, when the amount of the sulfide compound is too large, silver cannot be easily electrodeposited excessively on an object to be plated at the time of forming a SnAg alloy plating film, and there is a risk that it may be difficult to form the alloy composition in the SnAg alloy plating film as planned. For this reason, the amount of the sulfide compound in the SnAg alloy plating solution of the present embodiment should be an amount of 10 mol or less with respect to 1 mol of silver in the water-soluble silver compound.

The amount of the sulfide compound with respect to the entirety of the SnAg alloy plating solution is preferably in the range of 0.0001 mol/L or more and 2 mol/L or less, and more preferably in the range of 0.001 mol/L or more and 1 mol/L or less.

Furthermore, it is preferable that the amount of the sulfide compound in the SnAg alloy plating solution satisfies the following formula. In this case, since the number of sulfur atoms that can be easily coordinated with silver becomes equal or larger than the number of silver atoms, precipitation of silver becomes more difficult.

Number of sulfur atoms in one molecule of sulfide compound×number of moles of sulfide compound≥number of moles of silver.

The SnAg alloy plating solution of the present embodiment may further include an electrolyte, an oxidation inhibitor, a surfactant, a complexing agent for tin, a pH adjusting agent, and a gloss agent.

An electrolyte (free acid) has an action of increasing the electrical conductivity of the SnAg alloy plating solution. Examples of the electrolyte include hydrogen chloride, hydrogen bromide, sulfuric acid, an alkanesulfonic acid, an arylsulfonic acid, and an alkanolsulfonic acid. Specific examples of the alkanesulfonic acid include methanesulfonic acid and ethanesulfonic acid. Specific examples of the arylsulfonic acid include benzenesulfonic acid, phenolsulfonic acid, cresolsulfonic acid, and toluenesulfonic acid. Specific examples of the alkanolsulfonic acid include isethionic acid.

The electrolytes may be used singly, or two or more kinds thereof may be used in combination. The amount of addition of the electrolyte in the SnAg alloy plating solution of the present embodiment is generally in the range of 1 g/L or more and 600 g/L or less, and preferably in the range of 10 g/L or more and 400 g/L or less.

An oxidation inhibitor is intended to prevent oxidation of $Sn^{2+}$ in the SnAg alloy plating solution. Examples of the oxidation inhibitor include ascorbic acid or a salt thereof, hydroquinone, catechol, cresolsulfonic acid or a salt thereof, catecholsulfonic acid or a salt thereof, and hydroquinonesulfonic acid or a salt thereof. For example, in an acidic bath, hydroquinonesulfonic acid or a salt thereof is preferred, while in a neutral bath, ascorbic acid or a salt thereof is preferred.

The oxidation inhibitors may be used singly, or two or more kinds thereof may be used in combination. The amount of addition of the oxidation inhibitor in the SnAg alloy plating solution of the present embodiment is generally in the range of 0.01 g/L or more and 20 g/L or less, preferably in the range of 0.1 g/L or more 10 g/L or less, and more preferably in the range of 0.1 g/L or more and 5 g/L or less.

A surfactant has an effect of increasing the affinity between the SnAg alloy plating solution and an object to be plated, and also exerts effects such as an improvement in the external appearance of the plating film, an improvement in the adhesiveness to the object to be plated, and uniformization of the film thickness, by adsorbing on the surface of the plating film at the time of forming a SnAg alloy plating film, thereby suppressing the growth of crystals of the SnAg alloy within the plating film, and micronizing the crystals. Regarding the surfactant, various surfactants such as an anionic surfactant, a cationic surfactant, a nonionic surfactant, and an amphoteric surfactant can be used.

Specific examples of the anionic surfactant include an alkyl sulfate, a polyoxyethylene alkyl ether sulfate, a polyoxyethylene alkyl phenyl ether sulfate, an alkyl benzenesulfonate, and an alkyl naphthalenesulfonate. Specific examples of the cationic surfactant include a mono- to trialkylamine salt, a dimethyldialkylammonium salt, and a trimethylalkylammonium salt. Specific examples of the nonionic surfactant include an alkanol having 1 to 20 carbon atoms, phenol, naphthol, bisphenols, an alkylphenol having 1 to 25 carbon atoms, an arylalkylphenol, an alkyl naphthol having 1 to 25 carbon atoms, an alkoxy phosphoric acid (salt) having 1 to 25 carbon atoms, a sorbitan ester, a polyalkylene glycol, and a product obtained by addition condensation of 2 to 300 mol of ethylene oxide (EU) and/or propylene oxide (PO) to an aliphatic amide having 1 to 22 carbon atoms or the like. Specific examples of the amphoteric surfactant include carboxybetaine, imidazoline betaine, and an aminocarboxylic acid.

The surfactants may be used singly, or two or more kinds thereof may be used in combination. The amount of addition of the surfactant in the SnAg alloy plating solution of the present embodiment is generally in the range of 0.01 g/L or more and 50 g/L or less, preferably in the range of 0.1 g/L or more and 20 g/L or less, and more preferably in the range of 1 g/L or more and 10 g/L or less.

The SnAg alloy plating solution of the present embodiment is applicable to a plating bath of tin or a tin alloy in any arbitrary pH region such as an acidic pH, a weakly acidic pH, or a neutral pH. $Sn^{2+}$ ions are stable in acidity; however, these ions tend to easily undergo white precipitation at near neutrality. Therefore, in the case of applying the SnAg alloy plating solution of the present embodiment to a tin plating bath at near neutrality, it is preferable to add a complexing agent for tin to the SnAg alloy plating solution for the purpose of stabilizing $Sn^{2+}$ ions.

Regarding the complexing agent for tin, an oxycarboxylic acid, a polycarboxylic acid, and a monocarboxylic acid can be used. Specific examples include gluconic acid, citric acid, glucoheptonic acid, gluconolactone, acetic acid, propionic acid, butyric acid, ascorbic acid, oxalic acid, malonic acid, succinic acid, glycolic acid, malic acid, tartaric acid, and salts thereof. Preferred examples include gluconic acid, citric acid, glucoheptonic acid, gluconolactone, glucoheptolactone, and salts thereof. Furthermore, polyamines or aminocarboxylic acids, such as ethylenediamine, ethylenediaminetetraacetic acid (EDTA), diethylenetriaminepentaacetic acid (DTPA), nitrilotriacetic acid (NTA), iminodiacetic acid (IDA), iminodipropionic acid (IDP), hydroxyethylethylenediaminetriacetic acid (HEDTA), triethylenetetraminehexaacetic acid (TTHA), ethylenedioxybis(ethylamine)-N,N,N',N'-tetraacetic acid, glycines, nitrilotrimethylphosphonic acid, 1-hydroxyethane-1,1-diphosphonic acid, and salts of these are also effective as the complexing agent.

The complexing agent for tin may be used singly, or two or more kinds thereof may be used in combination. The amount of addition of the complexing agent for tin in the SnAg alloy plating solution of the present embodiment is generally in the range of 0.25 mol or more and 10 mol or less, preferably in the range of 0.25 mol or more and 5 mol or less, and more preferably in the range of 0.5 mol or more and 2 mol or less, with respect to 1 mol of tin in the water-soluble tin compound included in the SnAg alloy plating solution.

Examples of the pH adjusting agent include various acids such as hydrochloric acid and sulfuric acid; and various bases such as aqueous ammonia, potassium hydroxide, sodium hydroxide, and sodium hydrogen carbonate. Regarding the pH adjusting agent, monocarboxylic acids such as acetic acid and propionic acid; boric acids; phosphoric acids; dicarboxylic acids such as oxalic acid and succinic acid; and oxycarboxylic acids such as lactic acid and tartaric acid, are also effective.

Regarding the gloss agent, an aromatic carbonyl compound is preferred. An aromatic carbonyl compound has an effect of micronizing the crystallites of the SnAg alloy in the SnAg alloy plating film. An aromatic carbonyl compound is a compound in which a carbonyl group (—CO—X; provided that X means a hydrogen atom, a hydroxyl group, an alkyl group having a number of carbon atoms in the range of 1 or more and 6 or less, or an alkoxy group having a number of carbon atoms in the range of 1 or more and 6 or less) is bonded to a carbon atom of an aromatic hydrocarbon. An aromatic hydrocarbon includes a benzene ring, a naphthalene ring, and an anthracene ring. The aromatic hydrocarbon may have a substituent. Examples of the substituent include a halogen atom, a hydroxyl group, an alkyl group having a number of carbon atoms in the range of 1 or more and 6 or less, and an alkoxy group having a number of carbon atoms in the range of 1 or more and 6 or less. The carbonyl group may be directly bonded to the aromatic hydrocarbon, or may be bonded via an alkylene group having a number of carbon atoms in the range of 1 or more and 6 or less. Specific examples of the aromatic carbonyl compound include benzalacetone, cinnamic acid, cinnamaldehyde, and benzaldehyde.

The aromatic carbonyl compounds may be used singly, or two or more kinds thereof may be used in combination. The amount of addition of the aromatic carbonyl compound in the SnAg alloy plating solution of the present embodiment is generally in the range of 0.01 mg/L or more and 500 mg/L or less, preferably in the range of 0.1 mg/L or more and 100 mg/L or less, and more preferably in the range of 1 mg/L or more and 50 mg/L or less.

The SnAg alloy plating solution of the present embodiment can be produced by, for example, mixing a water-soluble tin compound, a water-soluble silver compound, a sulfide compound, and other components with water. In order to suppress oxidation of $Sn^{2+}$ ions and a reduction reaction of $Ag^+$ ions, it is preferable that the water-soluble silver compound is mixed in after the sulfide compound is introduced into a solution of the water-soluble tin compound.

Regarding the method for forming a SnAg alloy plating film using the SnAg alloy plating solution of the present embodiment, electroplating can be used.

It is preferable that formation of the SnAg alloy plating film by electroplating is carried out at a liquid temperature of 10° C. to 50° C. and a current density of 0.1 to 50 A/dm². More preferably, the formation is carried out at a liquid temperature of 20° C. to 30° C. and a current density of 1 to 20 A/dm².

When the SnAg alloy plating solution of the present embodiment configured as shown above is used, since the plating solution includes a sulfide compound represented by Formula (I) or Formula (II) shown above in an amount in the range of 0.25 mol or more and 10 mol or less with respect to 1 mol of silver in the water-soluble silver compound, even if the SnAg alloy plating solution is used or stored for a long time period, silver does not easily precipitate out as metal or an insoluble salt in the plating solution, and a SnAg alloy plating film can be stably formed.

EXAMPLES

Synthesis of Sulfide Compound

Synthesis Example 1

An aqueous sulfuric acid solution was prepared by mixing 200 g of concentrated sulfuric acid with 100 g of water. While this aqueous sulfuric acid solution was maintained under ice cooling at a temperature of 10° C. or lower, 18 g of 3,6-dithia-1,8-octanediol (Raw Material 1) was added thereto, and the mixture was mixed with stirring. While the mixed liquid thus obtained was continuously stirred under ice cooling, 1-(2-dimethylaminoethyl)-5-mercaptotetrazole (Raw Material 2) was added to the mixed liquid in an amount of 34 g (amount providing 2 mol with respect to 1 mol of Raw Material 1) for 30 minutes, and thus a reaction mixed liquid in which a sulfide compound had been produced was obtained. Subsequently, the temperature of the reaction mixed liquid was increased once to room temperature, subsequently the reaction mixed liquid was diluted with ice water, and then the sulfide compound was extracted with ether. The sulfide compound was dried using $MgSO_4$ and then was subjected to fractional distillation, and thereby a sulfide compound (A) represented by the following formula was obtained (yield: 83%).

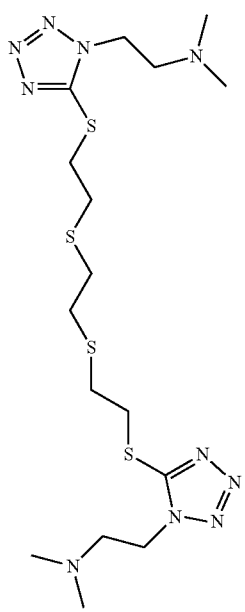

Sulfide compound (A)

Synthesis Example 2

187 g of 1,2-dibromoethane (Raw Material 1), 350 g of 1-(2-dimethylaminoethyl)-5-mercaptotetrazole (Raw Material 2) (amount providing 2 mol with respect to 1 mol of Raw Material 1), 400 mL of methanol, and 85 mL of pyridine were respectively introduced into a 1-L round bottom flask equipped with a stirrer and a reflux cooler. While the mixture was stirred, the mixture was subjected to boiling reflux for 16 hours, and then the resultant was cooled to 0° C. A sulfide compound precipitated out by cooling was filtered and washed, and thereby a sulfide compound (B) represented by the following formula was obtained (yield: 86%).

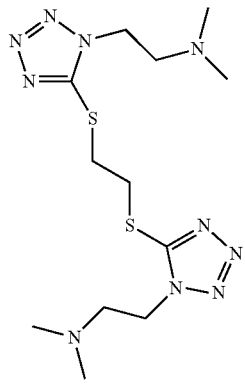

Sulfide compound (B)

Synthesis Examples 3 to 7

Sulfide compounds (C) to (G) represented by the following formulae were synthesized in the same manner as in Synthesis Example 1, except that the compounds shown in the following Table 1 were used as Raw Material 1 instead of 3,6-dithia-1,8-octanediol used in Synthesis Example 1, and the mixing ratio (molar ratio) of Raw Material 1 and Raw Material 2 [1-(2-dimethylaminoethyl)-5-mercaptotetrazole] was changed to the amounts shown in the following Table 1. The yields of the sulfide compounds thus obtained are shown in Table 1.

TABLE 1

| Synthesis Example | Product | Raw Material 1 | Raw Material 2 | Mixing ratio (molar ratio) Raw Material 1:Raw Material 2 | Yield (%) |
|---|---|---|---|---|---|
| Synthesis Example 1 | Sulfide compound (A) | 3,6-Dithia-1,8-octanediol | 1-(2-Dimethylaminoethyl)-5-mercaptotetrazole | 1:2 | 83 |
| Synthesis Example 3 | Sulfide compound (C) | 2-(Methylthio)ethanol | | 1:1 | 81 |
| Synthesis Example 4 | Sulfide compound (D) | 2,2'-Dithiodiethanol | | 1:2 | 80 |

TABLE 1-continued

| Synthesis Example | Product | Raw Material 1 | Raw Material 2 | Mixing ratio (molar ratio) Raw Material 1:Raw Material 2 | Yield (%) |
|---|---|---|---|---|---|
| Synthesis Example 5 | Sulfide compound (E) | 2,2'-Thiodiethanol | | 1:2 | 77 |
| Synthesis Example 6 | Sulfide compound (F) | 3,7-Dithia-1,9-nonanediol | | 1:2 | 75 |
| Synthesis Example 7 | Sulfide compound (G) | 2-(Benzylthio)ethanol | | 1:1 | 84 |

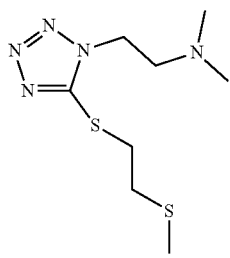

Sulfide compound (C)

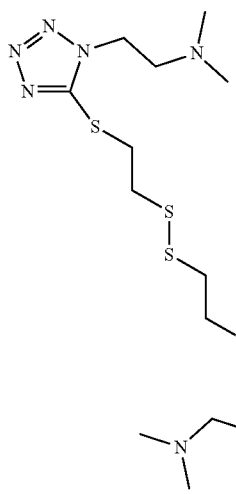

Sulfide compound (D)

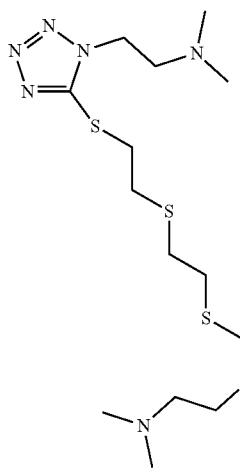

Sulfide compound (E)

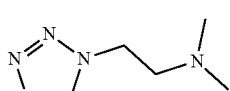

Sulfide compound (F)

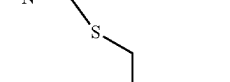

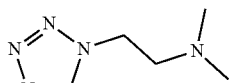

Sulfide compound (G)

Synthesis Examples 8 to 22

Sulfide compounds (H) to (V) represented by the following formulae were obtained in the same manner as in Synthesis Example 2, except that the compounds shown in the following Table 2 were used as Raw Material 1 instead of 1,2-dibromoethane used in Synthesis Example 2, and the mixing ratio (molar ratio) of Raw Material 1 and Raw Material 2 [1-(2-dimethylaminoethyl)-5-mercaptotetrazole] was changed to the amounts shown in the following Table 2. The yields of the sulfide compounds thus obtained are shown in Table 2.

TABLE 2

| Synthesis Example | Product | Raw Material 1 | Raw Material 2 | Mixing ratio (molar ratio) Raw Material 1:Raw Material 2 | Yield (%) |
|---|---|---|---|---|---|
| Synthesis Example 2 | Sulfide compound (B) | 1,2-Dibromoethane | 1-(2-Dimethylaminoethyl)-5-mercaptotetrazole | 1:2 | 86 |
| Synthesis Example 8 | Sulfide compound (H) | 1,2-Dichloroethylene | | 1:2 | 73 |
| Synthesis Example 9 | Sulfide compound (I) | 1,8-Dichlorooctane | | 1:2 | 70 |
| Synthesis Example 10 | Sulfide compound (J) | 1,2,3-Trichloropropane | | 1:3 | 62 |
| Synthesis Example 11 | Sulfide compound (K) | Pentaerythrityl tetrachloride | | 1:4 | 57 |
| Synthesis Example 12 | Sulfide compound (L) | 1,3-Dichloro-2-propanone | | 1:2 | 81 |
| Synthesis Example 13 | Sulfide compound (M) | 1,3-Dichloro-2-propanol | | 1:2 | 79 |
| Synthesis Example 14 | Sulfide compound (N) | 2,6-Dichloroaniline | | 1:2 | 72 |
| Synthesis Example 15 | Sulfide compound (O) | 2-Bromoethyl phenyl sulfide | | 1:1 | 86 |
| Synthesis Example 16 | Sulfide compound (P) | Bis(chloromethyl) sulfide | | 1:2 | 75 |
| Synthesis Example 17 | Sulfide compound (Q) | Chloromethylmethyl sulfide | | 1:1 | 75 |
| Synthesis Example 18 | Sulfide compound (R) | 2,5-Dichlorothiophene | | 1:2 | 67 |
| Synthesis Example 19 | Sulfide compound (S) | Chloromethyl chloroformate | | 1:2 | 69 |
| Synthesis Example 20 | Sulfide compound (T) | 4-Amino-2,6-dichloropyrimidine | | 1:2 | 72 |
| Synthesis Example 21 | Sulfide compound (U) | 2-Chloroethyl ether | | 1:2 | 65 |
| Synthesis Example 22 | Sulfide compound (V) | 1,2-Bis(2-chloroethoxy)ethane | | 1:2 | 59 |

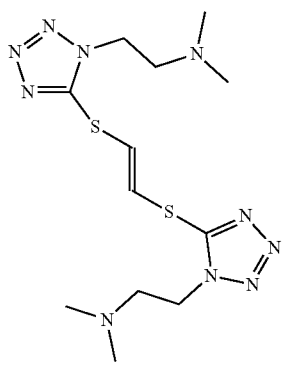

Sulfide compound (H)

-continued

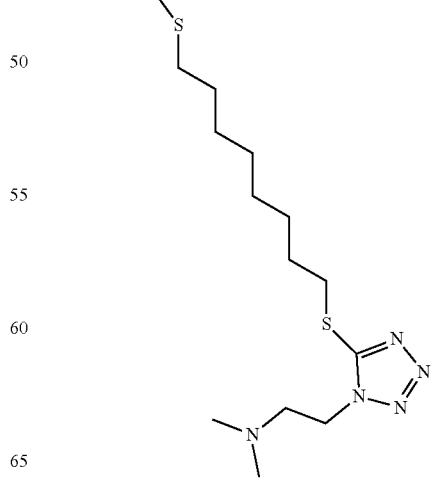

Sulfide compound (I)

Sulfide compound (J)
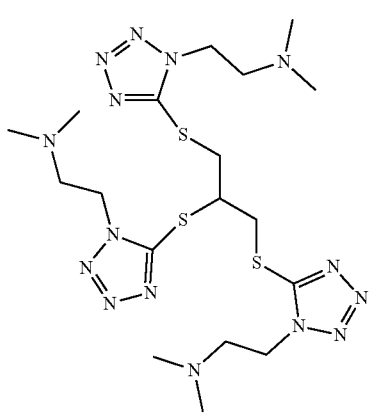
Sulfide compound (K)
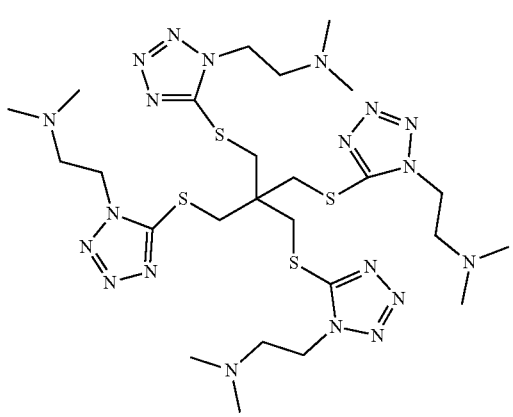
Sulfide compound (L)
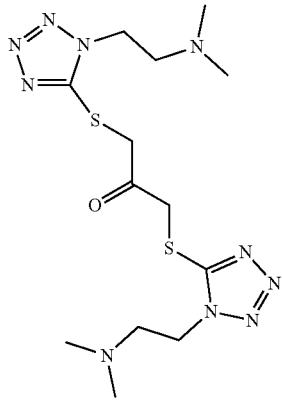
Sulfide compound (M)
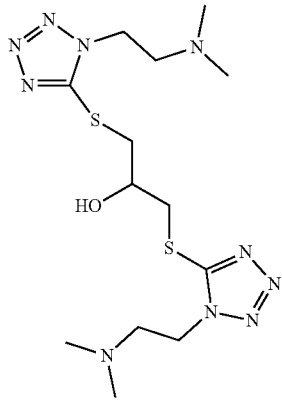
Sulfide compound (N)
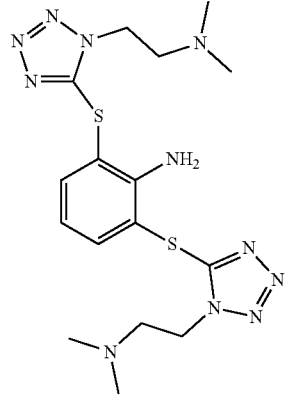
Sulfide compound (O)
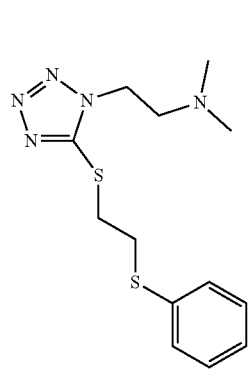
Sulfide compound (P)
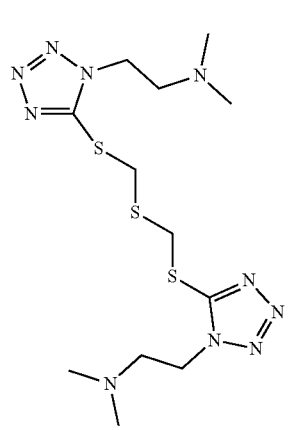
Sulfide compound (Q)
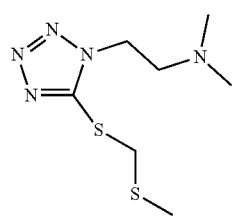

Sulfide compound (R)

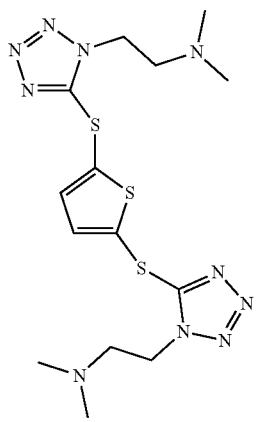

Sulfide compound (S)

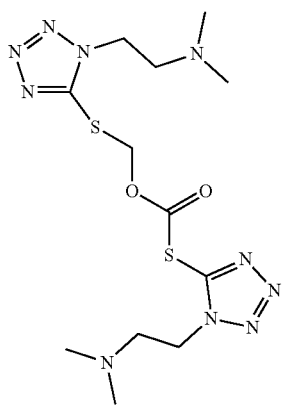

Sulfide compound (T)

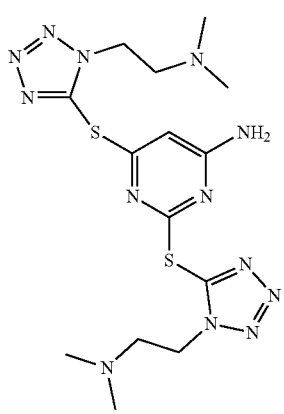

Sulfide compound (U)

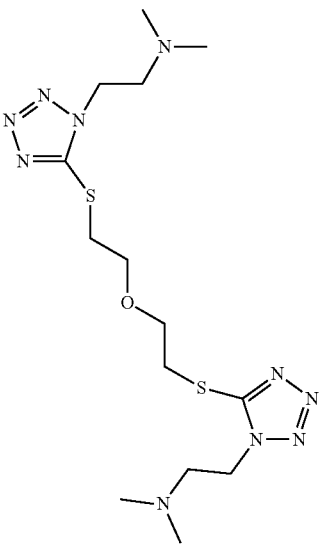

Sulfide compound (V)

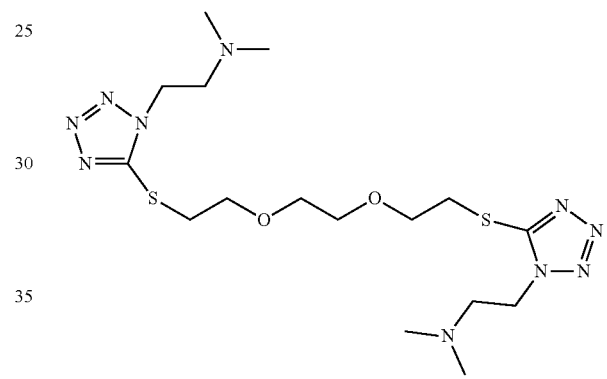

Examples 1 to 4 of the Present Invention and Comparative Examples 1 and 2

(Production of SnAg Alloy Plating Solution)

An aqueous solution of Sn methanesulfonate, catechol, and sulfide compound (A) or sulfide compound (B) were dissolved in methanesulfonic acid in the form of free acid, and then an aqueous solution of Ag methanesulfonate was added to the solution. Lastly, ion-exchanged water was added thereto, and thus a SnAg alloy plating solution having the composition shown in the following Table 3 was produced. The aqueous solution of Sn methanesulfonate and the aqueous solution of Ag methanesulfonate were prepared by electrolytically dissolving a Sn metal plate and an Ag metal plate, respectively, in an aqueous solution of methanesulfonic acid.

(Evaluation)

The SnAg alloy plating solution thus produced was introduced into a sealed glass bottle, and the plating solution was stored for one month at 50° C. in a clean oven manufactured by Panasonic Corporation. The external appearance of the SnAg alloy plating solution after the storage was inspected, and it was checked whether the transparency shown in the early stage of production was maintained. The results are presented in Table 3.

TABLE 3

| | Composition of SnAg alloy plating solution | | | | | | | Evaluation |
|---|---|---|---|---|---|---|---|---|
| | Sn methanesulfonate (as Sn$^{2+}$) | Ag methanesulfonate (as Ag$^+$) | Methanesulfonic acid (as free acid) | Catechol | Sulfide compound (A) With respect to 1 mol of Ag | Sulfide compound (B) With respect to 1 mol of Ag | Water | External appearance after storage |
| Example 1 of the present invention | 50 g/L | 0.5 g/L | 200 g/L | 1 g/L | 0.25 mol | — | Balance | Transparent |
| Example 2 of the present invention | | | | | 0.5 mol | — | Balance | Transparent |
| Example 3 of the present invention | | | | | 1 mol | — | Balance | Transparent |
| Example 4 of the present invention | | | | | — | 0.5 mol | Balance | Transparent |
| Comparative Example 1 | | | | | 0.1 mol | — | Balance | Blackened, precipitate produced |
| Comparative Example 2 | | | | | 0.2 mol | — | Balance | Blackened, precipitate produced |

From the evaluation results of Table 3, it was confirmed that stability to storage was enhanced by adding 0.25 mol or more of the sulfide compound (A) to 1 mol of Ag in the SnAg alloy plating solution. Furthermore, it was confirmed that stability to storage was also enhanced in the case of adding 0.5 mol of the sulfide compound (B) to 1 mol of Ag in the SnAg alloy plating solution. In this regard, it is speculated that since the sulfide compound (A) and the sulfide compound (B) have two or more sulfur atoms in one molecule, the sulfide compounds could stabilize Ag even if the amount of the sulfide compound was small with respect to Ag.

Example 5 of the Present Invention (Production of SnAg Alloy Plating Solution)

An aqueous solution of Sn methanesulfonate, catechol, and sulfide compound (A) were dissolved in methanesulfonic acid in the form of free acid, and then an aqueous solution of Ag methanesulfonate was added to the solution. Lastly, ion-exchanged water was added thereto, and thus a SnAg alloy plating solution having the following composition was produced.

Sn methanesulfonate: 50 g/L (as Sn$^{2+}$)

Ag methanesulfonate: 0.5 g/L (as Ag$^+$)

Methanesulfonic acid: 200 g/L (as free acid)

Catechol: 1 g/L

Sulfide compound (A): 2 mol (with respect to 1 mol of Ag)

Ion-exchanged water: Balance

Examples 6 to 26 of the Present Invention (Production of SnAg Alloy Plating Solution)

SnAg alloy plating solutions were produced in the same manner as in Example 5 of the present invention, except that sulfide compounds (B) to (V) were respectively added as complexing agents instead of the sulfide compound (A), in an amount providing 2 mol with respect to 1 mol of Ag.

Comparative Example 3

(Production of SnAg Alloy Plating Solution)

A SnAg alloy plating solution was produced in the same manner as in Example 5 of the present invention, except that 5-mercapto-1-phenyl-1H-tetrazole was added as a complexing agent instead of the sulfide compound (A), in an amount providing 2 mol with respect to 1 mol of Ag.

Comparative Example 4

(Production of SnAg Alloy Plating Solution)

A SnAg alloy plating solution was produced in the same manner as in Example 5 of the present invention, except that 1-(2-dimethylaminoethyl)-5-mercaptotetrazole was added as a complexing agent instead of the sulfide compound (A), in an amount providing 2 mol with respect to 1 mol of Ag.

Comparative Example 5

(Production of SnAg Alloy Plating Solution)

A SnAg alloy plating solution was produced in the same manner as in Example 5 of the present invention, except that 3,6-dithia-1,8-octanediol was added as a complexing agent instead of the sulfide compound (A), in an amount providing 2 mol with respect to 1 mol of Ag.

Comparative Example 6

(Production of SnAg Alloy Plating Solution)

A SnAg alloy plating solution was produced in the same manner as in Example 5 of the present invention, except that 2,2'-dithiodiethanol was added as a complexing agent instead of the sulfide compound (A), in an amount providing 2 mol with respect to 1 mol of Ag.

Comparative Example 7

(Production of SnAg Alloy Plating Solution)

A SnAg alloy plating solution was produced in the same manner as in Example 5 of the present invention, except that 1-(2-dimethylaminoethyl)-5-mercaptotetrazole and 3,6-dithia-1,8-octanediol were added as complexing agents instead of the sulfide compound (A), in an amount providing 1 mol each with respect to 1 mol of Ag.

(Evaluation)

For the SnAg alloy plating solutions produced in Examples 5 to 26 of the present invention and Comparative Examples 3 to 7, stability over time and electrolytic stability were evaluated as follows. The results are presented in Table 4 together with the type of the complexing agent added to the SnAg alloy plating solution.

(1) Stability Over Time

A SnAg alloy plating solution thus produced was introduced into a sealed glass bottle, and the plating solution was stored for 6 months at 50° C. in a clean oven manufactured by Panasonic Corporation. The Ag concentration dissolved in the SnAg alloy plating solution after the storage was analyzed using an ICP emission spectrometer. Then, the residual Ag amount was calculated by the following formula from the Ag concentration after the storage thus obtained.

Residual Ag Amount (%)=Ag Concentration after Storage/Ag Concentration Before Storage×100

(2) Electrolytic Stability

A SnAg alloy plating solution (10 L) thus produced was subjected to electrolysis by using a Pt plate as an anode and a SUS plate as a cathode under the conditions of 25° C. and 5 A/dm². An operation of replenishing tin and silver in the same amounts as the amounts lost by electrolysis at every 5 Ah/L was repeated, and electrolysis was continued to 200 Ah/L. The concentration of the complexing agent remaining in the SnAg alloy plating solution after the electrolysis was measured by the method shown below. Then, the residual Ag amount was calculated by the following formula from the concentration of the complexing agent after the electrolysis thus obtained.

Residual amount of complexing agent (%)=Concentration of complexing agent after electrolysis/concentration of complexing agent before electrolysis×100

(Method for Measuring Concentration of Complexing Agent)

The SnAg alloy plating solution that had been subjected to electrolysis was filtered with a disposable syringe. The concentration of the complexing agent in the filtrate thus obtained was measured using an HPLC apparatus manufactured by Shimadzu Corporation. MeOH was used as a mobile phase for the HPLC apparatus, an L-Column ODS that had been kept warm at 40° C. was used as a column, and measurement was carried out under the conditions of a flow rate of 1 mL/min and an injection amount of 10 μL.

TABLE 4

| | Type of complexing agent | Stability over time Residual Ag amount (%) | Electrolytic stability Residual complexing agent (%) |
|---|---|---|---|
| Example 5 of the present invention | Sulfide compound (A) | 98 | 93 |
| Example 6 of the present invention | Sulfide compound (B) | 93 | 93 |
| Example 7 of the present invention | Sulfide compound (C) | 96 | 97 |
| Example 8 of the present invention | Sulfide compound (D) | 97 | 93 |
| Example 9 of the present invention | Sulfide compound (F) | 93 | 82 |
| Example 10 of the present invention | Sulfide compound (F) | 91 | 89 |
| Example 11 of the present invention | Sulfide compound (G) | 96 | 88 |
| Example 12 of the present invention | Sulfide compound (H) | 94 | 86 |
| Example 13 of the present invention | Sulfide compound (I) | 94 | 88 |
| Example 14 of the present invention | Sulfide compound (J) | 93 | 85 |
| Example 15 of the present invention | Sulfide compound (K) | 97 | 89 |
| Example 16 of the present invention | Sulfide compound (L) | 91 | 84 |
| Example 17 of the present invention | Sulfide compound (M) | 92 | 86 |
| Example 18 of the present invention | Sulfide compound (N) | 90 | 83 |
| Example 19 of the present invention | Sulfide compound (O) | 96 | 93 |
| Example 20 of the present invention | Sulfide compound (P) | 94 | 91 |
| Example 21 of the present invention | Sulfide compound (Q) | 95 | 84 |
| Example 22 of the present invention | Sulfide compound (R) | 92 | 81 |
| Example 23 of the present invention | Sulfide compound (S) | 92 | 86 |
| Example 24 of the present invention | Sulfide compound (T) | 90 | 82 |
| Example 25 of the present invention | Sulfide compound (U) | 92 | 90 |
| Example 26 of the present invention | Sulfide compound (V) | 93 | 93 |
| Comparative Example 3 | 5-Mercapto-1-phenyl-1H-tetrazole | 56 | 41 |

TABLE 4-continued

| | Type of complexing agent | Stability over time Residual Ag amount (%) | Electrolytic stability Residual complexing agent (%) |
|---|---|---|---|
| Comparative Example 4 | 1-(2-Dimethylaminoethyl)-5-mercaptotetrazole | 48 | 47 |
| Comparative Example 5 | 3,6-Dithia-1,8-octanediol | 35 | 26 |
| Comparative Example 6 | 2,2'-Dithiodiethanol | 42 | 35 |
| Comparative Example 7 | 1-(2-Dimethylaminoethyl)-5-mercaptotetrazole 3,6-Dithia-1,8-octanediol | 58 | 46 |

From the evaluation results of Table 4, it can be seen that in all of the SnAg alloy plating solutions of Examples 5 to 26 of the present invention, all of which included a sulfide compound having a tetrazole group having two or more sulfur atoms and a dimethylaminoalkyl group as a complexing agent, the residual Ag amount after storage was high, such as 90% or higher, and the residual amount of the complexing agent after electrolysis was high, such as 80% or higher. Meanwhile, the SnAg alloy plating solutions including, as a complexing agent, a tetrazole having one sulfur atom (Comparative Example 3); a tetrazole having one sulfur atom and a dimethylaminoalkyl group (Comparative Example 4); a diol having two sulfur atoms (Comparative Example 5); an alcohol having two sulfur atoms (Comparative Example 6); or a tetrazole having one sulfur atom and a dimethylaminoalkyl group, and a diol having two sulfur atoms (Comparative Example 7), were such that in all cases, the residual Ag amount after storage was lower than 60%, and the residual amount of the complexing agent after electrolysis was lower than 50%.

From the evaluation results given above, it was confirmed that in the SnAg alloy plating solutions of Examples 5 to 26 of the present invention, silver cannot be easily precipitated out as an insoluble salt even if the plating solutions are used or stored for a long time period, and the plating solutions can stably form SnAg alloy plating films.

INDUSTRIAL APPLICABILITY

The SnAg alloy plating solution of the invention is such that silver is not easily precipitated out as metal or an insoluble salt in the plating solution even if the plating solution is used or stored for a long time period, and the plating solution can stably form a SnAg alloy plating film.

What is claimed is:
1. A SnAg alloy plating solution comprising:
a water-soluble tin compound;
a water-soluble silver compound; and
a water-soluble sulfide compound in an amount in the range of 0.25 mol or more and 10 mol or less with respect to 1 mol of silver in the water-soluble silver compound,
wherein the water-soluble sulfide compound is a compound represented by the following Formula (I) or Formula (II):

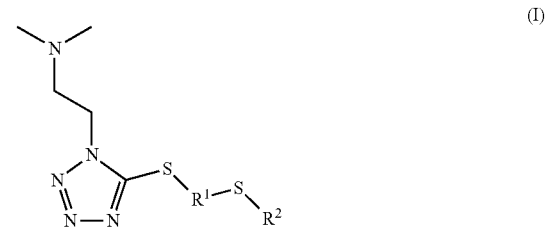

in Formula (I), $R^1$ represents a single bond or a divalent linking group; and $R^2$ represents one selected from the group consisting of a hydrogen atom, an alkyl group having a number of carbon atoms in a range of 1 to 8, a hydroxyalkyl group having a number of carbon atoms in a range of 1 to 8, an aryl group having a number of carbon atoms in a range of 6 to 18, and an aralkyl group having a number of carbon atoms in a range of 7 to 18, and

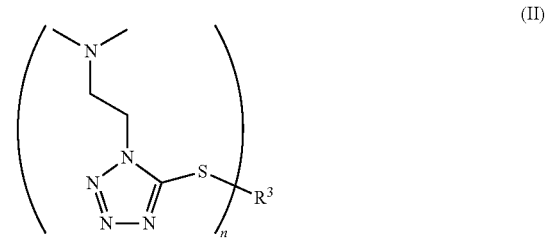

in Formula (II), n represents a number from 2 to 4;
in a case where n is 2, $R^3$ represents a divalent linking group,
in a case where n is 3, $R^3$ represents a trivalent linking group or a group containing the trivalent linking group and a divalent linking group linked to the trivalent linking group, and
in a case where n is 4, $R^3$ represents a tetravalent linking group or a group containing the tetravalent linking group and a divalent linking group linked to the tetravalent linking group, and wherein
the divalent linking group is: a hydrocarbon group selected from a group consisting of an alkylene group having a number of carbon atoms in a range of 1 to 8, an alkenylene group a number of carbon atoms in a range of 2 to 8, an alkynylene group having a number of carbon atoms in a range of 2 to 8 and a arylene group having a number of carbon atoms in a range of 6 to 18, with or without a substituent; the heterocyclic group that is a group in which two hydrogen atoms are removed from an aromatic or aliphatic heterocyclic group compound including a nitrogen atom, an oxygen atom, a sulfur atom or a phosphorous atom, with or without a substituent; or a combined group obtained by linking the hydrocarbon group and one or more of a carbonyl group (—CO—), an oxy group (—O—), a thio group (—S—), a sulfinyl group (—SO—), a sulfonyl group (—SO$_2$—), a —PO$_2$— group, a —CO—O— group, and a —CO—NR— group, the trivalent linking group is: a trivalent hydrocarbon group that is a group in which three hydrogen atoms are removed from a hydrocarbon compound selected from a group consisting of an alkane having a number of carbon atoms in a range of 1 to 8, an alkene having a number of carbon atoms in a range of 2 to 8, an alkyne having a number of carbon atoms in a range of 2 to 8 and an aromatic hydrocarbon having a number of carbon atoms in a range of 6 to 18, with or without a substituent; or a trivalent heterocyclic group that is the group in which three hydrogen atoms are removed from aromatic or aliphatic heterocyclic compound including a nitrogen atom, an oxygen atom, a sulfur atom or a phosphorous atom, with or without a substituent, and the tetravalent linking group is: a tetravalent hydrocarbon group that is a group in which four hydrogen atoms are removed from a hydrocarbon compound selected from a group consisting of an alkane having a number of carbon atoms in a range of 1 to 8, an alkene having a number of carbon atoms in a range of 2 to 8, an alkyne having a number of carbon atoms in a range of 2 to 8 and an aromatic hydrocarbon having a number of carbon atoms in a range of 6 to 18, with or without a substituent; or a tetravalent heterocyclic group that is the group in which four hydrogen atoms are removed from aromatic or aliphatic heterocyclic compound including a nitrogen atom, an oxygen atom, a sulfur atom or a phosphorous atom, with or without a substituent, and wherein the substituent in the divalent linking group, the trivalent linking group and the tetravalent linking group is: a halogen atom; a hydroxyl group; an amino group; an alkyl group having a number of carbon atoms in a range of 1 to 8; an aryl group having a number of carbon atoms in a range of 6 to 18; an aralkyl group having a number of carbon atoms in a range of 7 to 30; or an alkoxy group having a number of carbon atoms in a range of 1 to 8.

2. The SnAg alloy plating solution according to claim 1, wherein the water-soluble sulfide compound is a compound represented by Formula (I).

3. The SnAg alloy plating solution according to claim 1, wherein the water-soluble sulfide compound is a compound represented by Formula (II), n is 2, and $R^3$ is the divalent linking group.

4. The SnAg alloy plating solution according to claim 1, wherein the water-soluble sulfide compound is: a compound represented by Formula (II), n is 3, and $R^3$ is the trivalent linking group; or a group containing the trivalent linking group and the divalent linking group linked to the trivalent linking group.

5. The SnAg alloy plating solution according to claim 1, wherein the water-soluble sulfide compound is: a compound represented by Formula (II), n is 4, and $R^3$ is the tetravalent linking group; or a group containing the tetravalent linking group and the divalent linking group linked to the tetravalent linking group.

* * * * *